(12) United States Patent
Watson et al.

(10) Patent No.: US 8,288,441 B2
(45) Date of Patent: Oct. 16, 2012

(54) COMPOSITIONS COMPRISING A PHYSIOLOGICAL COOLANT

(75) Inventors: Michael Steven Watson, Basingstoke (GB); Stephen David Watkins, Ashford (GB); Sander Tondeur, Loosdrecht (NL)

(73) Assignee: Givaudan Nederland Services B.V., Naarden (NL)

( * ) Notice: Subject to any disclaimer, the term of this patent is extended or adjusted under 35 U.S.C. 154(b) by 0 days.

(21) Appl. No.: 12/529,462

(22) PCT Filed: Mar. 3, 2008

(86) PCT No.: PCT/EP2008/001644
§ 371 (c)(1),
(2), (4) Date: Jul. 28, 2010

(87) PCT Pub. No.: WO2008/107137
PCT Pub. Date: Sep. 12, 2008

(65) Prior Publication Data
US 2010/0292294 A1    Nov. 18, 2010

(30) Foreign Application Priority Data
Mar. 2, 2007  (GB) .................................. 0704163.5

(51) Int. Cl.
*A01N 37/18* (2006.01)
*A61K 31/16* (2006.01)
(52) U.S. Cl. ...................................... 514/614
(58) Field of Classification Search .................... 514/614
See application file for complete search history.

(56) References Cited

U.S. PATENT DOCUMENTS

| | | | |
|---|---|---|---|
| 6,267,974 B1 | 7/2001 | Suares et al. | |
| 6,897,195 B2 * | 5/2005 | Su et al. | 512/1 |
| 7,001,594 B1 * | 2/2006 | Peffly et al. | 424/70.1 |

FOREIGN PATENT DOCUMENTS

| | | |
|---|---|---|
| EP | 1197205 A2 | 4/2002 |
| WO | 03043431 A1 | 5/2003 |
| WO | 2005049553 A1 | 6/2005 |
| WO | 2005102071 A1 | 11/2005 |
| WO | 2006125334 A1 | 11/2006 |
| WO | 2006130710 A1 | 12/2006 |
| WO | 2007019719 A1 | 2/2007 |

OTHER PUBLICATIONS

Erman, Progress in Physiological Cooling Agents, Perfumer & Flavorist, Nov./Dec. 2004, pp. 34-50, vol. 29.
Leffingwell, Cool Without Menthol & Cooler than Menthol and Cooling Compounds as Insect Repellents, Leffingwell & Associates, http://www.leffingwell.com/cooler_than_menthol.htm, 2006, updated 2009.

* cited by examiner

*Primary Examiner* — Benjamin Packard
(74) *Attorney, Agent, or Firm* — The Webb Law Firm

(57) ABSTRACT

The present invention concerns enhancements in the cooling effects of certain physiological coolant-containing compositions such as topically applied cosmetic, toiletry or pharmaceutical products, wherein the cooling effect of the physiological coolants is enhanced by the addition of a substance according to formula (I) or dermatologically acceptable salts thereof:

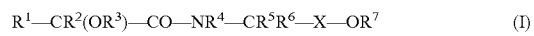

$$R^1-CR^2(OR^3)-CO-NR^4-CR^5R^6-X-OR^7 \quad (I)$$

It was found that substances represented by formula (I) are capable of bringing about greater cooling effects from reduced concentrations of physiological coolants without behaving as physiological coolants themselves, thereby enabling the preparation of compositions that do not necessarily have the characteristic minty odor of menthol-containing products and/or to allow greater freedom in creating perfumed products.

6 Claims, No Drawings

COMPOSITIONS COMPRISING A PHYSIOLOGICAL COOLANT

FIELD OF THE INVENTION

The present invention concerns improvement in the cooling effects of compositions such as topically applied cosmetics, toiletries and pharmaceutics.

BACKGROUND OF THE INVENTION

Physiological cooling agents are used in topical formulations to impart a cooling sensation to the skin. These do not actually cool the skin temperature but interact with the cold and hot receptors present in the skin to give the individual the perception of a cool or warm feeling. The exact mechanism of the interaction between the cooling agent and the nerve receptors is not fully understood but, without wishing to be bound by theory, it is believed that physiological cooling agents affect calcium channels or the calcium transport associated with a number of receptors found in the skin. This interaction causes a greater stimulation of the nerve receptors giving rise to the perception of cold or hot.

Menthol is probably the best known of all the physiological cooling agents and is obtained from various species of mint plant (e.g. *Mentha arvensis*). Menthol is relatively cheap and effective but has the disadvantage that it has a strong mint-like odour. In addition, the cooling or warming lasts for a relatively short period of time when applied to skin, typically, one or two hours.

A number of compounds have been developed based on the structure of menthol or using the structure and/or the cooling effect of menthol as a guide to the synthesis of a new cooling compound. Such synthetic physiological cooling agents include: menthol esters, menthol ethers, menthone derivatives, menthane derivatives, etc. These compounds have the advantage that they do not tend to have a mint-like odour and so are more pleasant to use; the topically applied product and the skin do not have to smell of mint to provide a cooling sensation.

A number of recent articles have reviewed ingredients claimed to provide a skin cooling sensation:
- "Progress in Physiological Cooling agents", Mark Ermann, Perfumery & Flavourist, Vol. 29, November/December 2004
- "Cool Without Menthol & Cooler than Menthol and Cooling Compounds as Insect Repellents", John C. Leffingwell, Leffingwell & Associates, 2006

In order to obtain a strong cooling effect on the skin, quite high levels of physiological cooling agents need to be incorporated into the topically applied formulation. Menthol, being one of the more effective cooling agents, is often used from around 0.01% w/w upwards in the formulation. Synthetic cooling agents based around the activity of menthol, such as those mentioned above, are used at higher levels, typically 0.05% w/w and upwards and often up to 2%. Since these synthetic cooling agents are expensive, there is a need to find ways to enhance their perceived cooling effect on the skin.

SUMMARY OF THE INVENTION

Accordingly, in a first aspect, the present invention provides a composition comprising a physiological coolant and one or more coolant-enhancing substances according to formula (I), and/or physiologically- or dermatologically-acceptable salts thereof:

$$R^1\text{—}CR^2(OR^3)\text{—}CO\text{—}NR^4\text{—}CR^5R^6\text{—}X\text{—}OR^7 \qquad (I)$$

wherein:

X represents a covalently bound radical selected from the group comprising $C_1$-$C_5$ alkyl or $C_2$-$C_5$ alkenyl, each optionally substituted with 1-4 substituents selected from hydroxyl, $C_1$-$C_3$ alkyl and $C_1$-$C_3$ alkenyl;

$R^1$ and $R^2$ independently represent hydrogen; or $C_1$-$C_8$ alkyl, $C_2$-$C_8$ alkenyl or $C_3$-$C_8$ cycloalkyl, each optionally substituted with 1-8, preferably 1-6, substituents selected from hydroxyl, oxo, $C_1$-$C_3$ alkyl; $C_2$-$C_3$ alkenyl and $C_1$-$C_3$ carboxyl;

$R^3$ represents hydrogen, $C_1$-$C_3$ acyl or $C_1$-$C_3$ alkyl;

$R^4$ represents hydrogen; or $C_1$-$C_6$ alkyl, $C_2$-$C_6$ alkenyl, $C_3$-$C_6$ cycloalkyl, $C_3$-$C_6$ cycloalkenyl or $C_1$-$C_6$ acyl, each optionally substituted with 1-6 substituents selected from hydroxyl, $C_1$-$C_3$ alkyl and $C_2$-$C_3$ alkenyl;

$R^5$ and $R^6$ independently represent hydrogen; hydroxyl; or $C_1$-$C_8$ alkyl, $C_2$-$C_8$ alkenyl, or $C_3$-$C_8$ cycloalkyl, each optionally substituted with 1-8 substituents selected from hydroxyl, $C_1$-$C_3$ alkyl and $C_2$-$C_3$ alkenyl;

$R^7$ represents hydrogen, $C_1$-$C_3$ acyl, $C_1$-$C_3$ alkyl, a phosphate group selected from mono-, di- and triphosphate or a $C_2$-$C_5$ carboxyacyl, optionally further substituted with 1-3 substituents selected from hydroxyl, oxo, $C_1$-$C_3$ carboxyl; provided that $R^1$—$CR^2(OR^3)$—CO— does not represent a hexose or heptose sugar acid residue comprising more than four hydroxyl groups.

DETAILED DESCRIPTION OF THE INVENTION

The present inventors have surprisingly found that substances represented by the following formula (I) can be used advantageously to improve the cooling effect of compositions such as, for example, cosmetics, toiletries and pharmaceutical products:

$$R^1\text{—}CR^2(OR^3)\text{—}CO\text{—}NR^4\text{—}CR^5R^6\text{—}X\text{—}OR^7 \qquad (I)$$

This is surprising, given that these materials do not act as a physiological coolant when used in isolation.

The present inventors found that the coolant-enhancing substances according to the present invention are particularly useful in a wide variety of topical applications, of which skin creams, lotions, gels, deodorant sticks and deodorant sprays are non-limiting examples.

Therefore, the present invention relates to topically applied cosmetic compositions, toiletries and pharmaceutical products comprising at least one substance according to formula (I) and at least one physiological coolant.

Furthermore, the present invention relates to the use of the substances according to formula (I) for improving the cooling effect of topically applied cosmetics, toiletries and pharmaceutical products.

Accordingly, in a first aspect, the present invention provides a composition comprising a physiological coolant and one or more coolant-enhancing substances according to formula (I), and/or physiologically- or dermatologically-acceptable salts thereof.

In a second aspect, the invention provides a method of providing a cooling sensation to the skin, the method comprising topically applying a composition according to the invention to the skin.

In a third aspect, the invention provides the use of a substance according to formula (I) or dermatologically acceptable salts thereof, to enhance the cooling effect of physiological coolant-containing compositions.

In formula (I), $R^7$ preferably represents hydrogen, $C_1$-$C_3$ acyl, $C_1$-$C_3$ alkyl or a phosphate group selected from mono-, di- and triphosphate, more preferably hydrogen or a phosphate group as defined above.

More preferably, X represents $C_1$-$C_5$ alkyl, $C_2$-$C_5$ alkenyl, each optionally substituted with 1-4 hydroxyl groups; $R^1$ and $R^2$ independently represent hydrogen; or $C_1$-$C_5$ alkyl or $C_2$-$C_5$ alkenyl, each optionally substituted with 1-5 substituents selected from hydroxyl, oxo and $C_1$-$C_3$ carboxyl; $R^3$ represents hydrogen; $R^4$ represents hydrogen; or $C_1$-$C_6$ alkyl, $C_2$-$C_6$ alkenyl or $C_1$-$C_6$ acyl, each optionally substituted with 1-6 hydroxyl groups; $R^5$ and $R^6$ independently represent hydrogen, hydroxyl or $C_1$-$C_8$ alkyl or $C_2$-$C_8$ alkenyl, each substituted with 1-8 hydroxyl groups and $R^7$ represents hydrogen, a phosphate group selected from mono-, di-, and triphosphate or a $C_2$-$C_5$ carboxyacyl, optionally further substituted with 1-3 substituents selected from hydroxyl, oxo or $C_1$-$C_3$ carboxyl.

Still more preferably, X represents $C_1$-$C_2$ alkyl, optionally substituted with a hydroxyl group; $R^1$ and $R^2$ independently represent hydrogen or $C_1$-$C_5$ alkyl substituted with 1-5 substituents selected from hydroxyl, oxo and $C_1$-$C_3$ carboxyl; $R^4$ represents hydrogen; or $C_1$-$C_6$ alkyl, $C_2$-$C_6$ alkenyl or $C_1$-$C_6$ acyl, each optionally substituted with 1-6 hydroxyl groups; $R^5$ and $R^6$ independently represent hydrogen or $C_1$-alkyl substituted with a hydroxyl group; $R^3$ represents hydrogen; $R^7$ represents hydrogen, a phosphate group selected from mono-, di-, and triphosphate or a $C_2$-$C_5$ carboxyacyl optionally further substituted with 1-3 substituents selected from hydroxyl, oxo, $C_1$-$C_3$ carboxyl.

The present inventors have found that the substances defined here above are very useful ingredients which, in the presence of one or more physiological coolant substances, are capable of imparting highly appreciated cooling sensations to the products in which they are incorporated whilst not behaving as physiological coolants when used in isolation.

Because the coolant-enhancing substances according to the invention are not particularly volatile, they do not produce a strong fragrance impact. However, the enhanced coolant effects observed in compositions comprising the inventive substances allow lower concentrations of physiological coolants to be used, thereby freeing a skilled formulator to prepare compositions that do not have the characteristic minty odour of menthol-containing products and/or to allow greater freedom in creating perfumed products, or enable cost reductions to be made by lowering the concentrations of other, more expensive, physiological coolants.

It was found that particularly satisfying results can be obtained with coolant-enhancing substances according to formula (I) wherein X represents a covalently bound $C_1$-$C_4$ alkyl or $C_2$-$C_4$ alkenyl chain, each optionally substituted with 1-2 substituents selected from hydroxyl and $C_1$-$C_2$ alkyl. More preferably, X represents a $C_1$-$C_3$ alkyl chain, optionally substituted with hydroxyl or methyl. Even more preferably, X represents a $C_1$-$C_2$ alkyl chain. Most preferably it represents methyl.

Alternatively, $R^1$ and $R^2$ independently represent hydrogen or $C_1$-$C_4$ alkyl optionally substituted with 1-5 substituents selected from hydroxyl and oxo, even more preferably $R^1$ represents hydrogen, methyl, —$CH_2$—COOH, or —CHOH—COOH and $R^2$ represents hydrogen or —$CH_2$—COOH, such that the coolant-enhancing substances comprise primary amine derivatives of organic food acids, preferably organic acids selected from lactic acid, malic acid, citric acid, glycolic acid and tartaric acid, more preferably tartaric acid and lactic acid.

In still another preferred embodiment $R^1$ represents $C_1$-$C_4$ alkyl, more preferably $C_1$-$C_2$ alkyl, most preferably methyl.

A particularly preferred combination is where $R^1$ represents hydrogen and $R^2$ represents methyl.

In the aforementioned formula (I) $R^4$ preferably represents hydrogen or $C_1$-$C_4$ alkyl, most preferably hydrogen. Likewise, $R^5$ preferably represents hydrogen or $C_1$-$C_3$ alkyl. Most preferably it represents hydrogen.

Alternatively, it is preferred that $R^4$ represents $C_1$-$C_4$ alkyl substituted with 1-3 hydroxyl groups, more preferably $R^4$ represents 2-hydroxyethyl. In a particularly preferred embodiment $R^4$ represents 2-hydroxyethyl, X represents methyl and $R^5$ and $R^6$ represent hydrogen, such that the coolant-enhancing substances comprise one or more α-hydroxy carboxylic acid derivatives of diethanolamine.

In still another equally preferred embodiment, $R^1$, $R^2$, $R^3$ and W are chosen such that formula (I) represents a tertiary amine comprising two identical α-hydroxycarboxylic acid residues.

It is generally preferred that $R^2$ represents hydrogen or $C_1$-$C_4$ alkyl, preferably hydrogen.

According to still another preferred embodiment of the invention X represents methylene, —CHOH—$CH_2$, or ethylene and $R^5$ and $R^6$ independently represent methyl, hydroxymethyl or hydrogen. Preferably X represents methylene and $R^5$ and $R^6$ represents hydrogen. In an even more preferred embodiment $R^5$, $R^6$ and X together comprise 2 carbon atoms such that the coolant-enhancing substances comprise α-hydroxy carboxylic acid derivatives of amino-propanols and amino-propanediols.

It was found that coolant-enhancing substances according to the present invention wherein $R^7$ represents a substituent that is easily deprotonated in aqueous media provide particularly satisfying results. Hence, according to an alternative embodiment $R^7$ represents a $C_2$-$C_5$ carboxyacyl, optionally substituted with optionally further substituted with 1-3 substituents selected from hydroxyl, oxo, $C_1$-$C_3$ carboxyl, such that monoesters of di and tri-carboxylic acids are provided, preferably di- or tricarboxylic acids selected from fumaric acid, tartaric acid, malic acid, citric acid, and aconitic acid.

In another preferred embodiment, $R^2$ and/or $R^5$ represent hydrogen. Most preferably, both $R^2$ and $R^5$ represent hydrogen.

Preferred coolant-enhancing substances are selected from the group consisting of N-lactoyl ethanolamide, N-Lactoyl ethanolamide phosphate, N-α-hydroxy-butanoyl ethanolamide, N-α-hydroxy-butanoyl ethanolamide phosphate, N-lactoyl diethanolamide, N-lactoyl-2-amino-1,3-propanediol, N-lactoyl-3-amino-1,2-propanediol, N-lactoyl-3-amino-1-propanol, N-gluconyl-2-amino-1,3-propanediol, N-gluconyl-3-amino-1,2-propanediol, N-mannonyl ethanolamide, N-glycoyl ethanolamide, 2-hydroxyethyl-N-tartaramide, 2-hydroxyethyl-N-malamide or 2-hydroxyethyl-N-citramide.

Preferably the present coolant-enhancing substance is selected from the group consisting of N-lactoyl ethanolamide, N-lactoyl ethanolamide phosphate and N-α-hydroxybutanoyl ethanolamide, more preferably N-lactoyl ethanolamide.

Suitable physiological coolants include but are not limited to: menthol, menthyl Pyrrolidone carboxylate, menthyl lactate, isopulegol, menthone, N-ethyl p-menthanecarboxamide (WS-3), N,2,3-trimethyl-2-isopropylbutanamide (WS-23), ethyl 2-(2-isopropyl-5methylcyclohexanecarboxamido)-acetate (WS-5), menthone glycerine acetal (Frescolat® MGA), mono-menthyl succinate (Physcool®), mono-menthyl glutarate, O-menthyl glycerine (CoolAct® 10) and 2-sec-butylcyclohexanone (Freskomenthe®), menthane, camphor, pulegol, cineol, mint oil, peppermint oil, spearmint oil, eucalyptus oil, 3-1-menthoxypropane-1,2-diol, 3-1-menthoxy-2-methylpropane-1,2-diol, p-menthane-3,8-diol, 2-1-menthoxyethane-1-ol, 3-1-menthoxypropane-1-ol, and 4-1-menthoxybutane-1-ol, or mixtures thereof. Further examples of cooling compounds can be found e.g. in WO2005/049553 (US2006/0276667A1) (e.g. 2-isopropyl-5-methyl-cyclohexanecarboxylic acid (4-cyanomethyl-phenyl)-amide and 2-isopropyl-5-methyl-cyclohexanecarboxylic acid (4-cyanophenyl)-amide), WO2006/125334 (e.g. 4-[(2-isopropyl-5-methyl-cyclohexanecarbonyl)-amino]-benzamide, 3-[(2-isopropyl-5-methyl-cyclohexanecarbonyl)-amino]benzamide, and (2-isopropyl-5-methyl-N-(4-(4-methylpiperazine-1-carbonyl)phenyl)cyclohexanecarboxamide) and WO2007/019719 (e.g. 2-isopropyl-5-methyl-cyclohexanecarboxylic acid pyridin-2-ylamide, and 2-isopropyl-5-methyl-cyclohexanecarboxylic acid (2-pyridin-2-yl-ethyl)-amide), which are incorporated herein by reference.

Preferably the physiological coolant is selected from the group consisting of menthyl Pyrrolidone carboxylate, menthyl lactate, menthoxy propanediol, menthlone glycerol ketal, isopulegol, methyl di-isopropyl propionamide and ethyl menthane carboxamide and combinations thereof.

The compositions according to the invention are preferably topically applied cosmetic, toiletry or pharmaceutical compositions, more preferably cosmetic compositions. It is preferred that the compositions are unsuitable for use in the human mouth.

For the present invention, the term "pharmaceutics" refers to products such as those used to impart warmth or cooling to, for example, regions of articular or muscular discomfort or to give relief from the symptoms of fever, nasal congestion etc., but excludes all systemic preparations.

The compositions suitably comprise at least 0.01 wt % of one or more physiological coolant and one or more of the coolant-enhancing substances as defined herein in an amount of at least 0.005 wt. %, more preferably at least 0.05 wt. %. Preferably the amount of the present coolant-enhancing substances does not exceed 20 wt. %, more preferably it does not exceed 10 wt. %, and most preferably it does not exceed 5%.

Typically, in the compositions according to the invention, the coolant-enhancing substances and physiological coolants substances as defined herein before are employed in a weight ratio within the range of 2000:1 to 1:200, more preferably in a weight ratio of between 20:1 and 1:2, and most preferably in a weight ratio of between 20:1 and 2:5.

The compositions according to the present invention may suitably be prepared in any convenient form. In one preferred embodiment compositions are provided comprising N-Lactoyl ethanolamide as well as menthyl pyrrolidone carboxylate, also known as menthyl PCA. Menthyl PCA is available from Quest International under the trade name Questice®.

In another preferred embodiment of the present invention compositions are provided comprising N-Lactoyl ethanolamide as well as menthol.

In still another preferred embodiment compositions are provided comprising N-Lactoyl ethanolamide as well as other physiological cooling agents, such as menthyl lactate, menthyl glyceryl ether, menthone glyceryl ketal, and the like.

These examples are for the purpose of illustration only and it is understood that variations and modifications can be made by one skilled in the art without departing from the spirit and the scope of the invention. It should be understood that the embodiments described are not only in the alternative, but can be combined.

Example 1

A simple aqueous ethanol solution (50:50) containing 1% by weight of lactoyl ethanolamide was applied to one forearm. The aqueous ethanol solution alone (control) was then applied to the other forearm at a similar dosage, and the perception of cooling from either arm noted. This was repeated on 10 volunteers in total.

The results showed no difference in cooling perception between the test solution, containing lactoyl ethanolamide, and the placebo solution.

Example 2

A simple aqueous ethanol solution (50:50) containing 0.2% by weight of L-menthol and 1% by weight of lactoyl ethanolamide was applied to one forearm at a concentration of 2 drops per 10 square centimetres of skin. The aqueous ethanol solution containing just 0.2% by weight L-menthol was then applied to the other forearm at the same dose, and the perception of cooling from either arm noted. This was repeated on 10 volunteers.

The results showed a higher cooling perception was felt from the solution containing lactoyl ethanolamide.

Example 3

A simple aqueous ethanol solution (50:50) containing 0.2% by weight of L-menthol and 0.5% by weight of lactoyl ethanolamide was applied to one forearm at a concentration of 2 drops per 10 square centimetres of skin. The aqueous ethanol solution containing 0.2% by weight L-menthol was then applied to the other forearm at the same dose, and the perception of cooling from either arm noted over 4 hours at 30 minute intervals. This was repeated on 12 volunteers.

The results showed a higher cooling perception was felt from the solution containing L-menthol and lactoyl ethanolamide. In addition, the cooling was felt over a longer period of time (for over 3 hours) with the solution containing L-menthol and lactoyl ethanolamide. The solution containing just L-menthol provided a cooling sensation for only about 2 hours.

Example 4

A simple aqueous ethanol solution (50:50) containing 1% by weight of menthyl lactate and 1% by weight of lactoyl ethanolamide was applied to one forearm at a concentration of 2 drops per 10 square centimetres of skin. The aqueous ethanol solution containing 1% by weight menthyl lactate was then applied to the other forearm at the same dose, and the perception of cooling from either arm noted over 4 hours at 30 minute intervals. This was repeated on 12 volunteers.

The results showed a higher cooling perception was felt from the solution containing menthyl lactate and lactoyl ethanolamide. In addition, the cooling was felt over a longer period of time (for over 3 hours) with the solution containing menthyl lactate and lactoyl ethanolamide. The solution containing just menthyl lactate provided a cooling sensation for only about 2 hours.

Example 5

A simple aqueous ethanol solution (50:50) containing 1.0% by weight of menthone glyceryl ketal and 0.5% by weight of lactoyl ethanolamide was applied to one forearm at a concentration of 2 drops per 10 square centimetres of skin.

The aqueous ethanol solution containing 1% by weight menthone glyceryl ketal was then applied to the other forearm at the same dose, and the perception of cooling from either arm noted over 4 hours at 1 hour intervals. This was repeated on 10 volunteers.

The results showed a higher cooling perception was felt from the solution containing menthone glyceryl ketal and lactoyl ethanolamide. In addition, the cooling was felt over a longer period of time (for over 4 hours) with the solution containing menthone glyceryl ketal and lactoyl ethanolamide. The solution containing just menthone glyceryl ketal provided a cooling sensation for only about 3 hours.

Example 6

A simple aqueous ethanol solution (50:50) containing 0.75% by weight of menthyl glyceryl ether and 0.5% by weight of lactoyl ethanolamide was applied to one forearm at a concentration of 2 drops per 10 square centimetres of skin. An aqueous ethanol solution containing 1% by weight menthyl glyceryl ether was then applied to the other forearm at the same dose, and the perception of cooling from either arm noted over a 4 hour period. This was repeated on 12 volunteers.

The results showed a similar cooling perception was felt from the two solutions; the addition of lactoyl ethanolamine allows the reduction of the expensive physiological coolant, in this case menthyl glyceryl ether.

Example 7

A simple aqueous ethanol solution (50:50) containing 1% by weight of menthyl pyrrolidone carboxylate and 0.5% by weight of lactoyl ethanolamide was applied to one forearm at a concentration of 2 drops per 10 square centimetres of skin. An aqueous ethanol solution containing 1% by weight menthyl pyrrolidone carboxylate was then applied to the other forearm at the same dose and the perception of cooling from either arm noted over a 6 hour period. This was repeated on 33 volunteers.

The results showed a higher level of cooling was obtained with the presence of lactoyl ethanolamine and that the improved cooling perception was sustained for at least 6 hours.

Example 8

Cooling Liquid Talc

A light, moisturising lotion containing talc and a physiological coolant to keep you dry and fresh all day.

| Formulation: | % w/w |
| --- | --- |
| Water | to 100.00 |
| Menthyl Pyrrolidone Carboxylate | 2.00 |
| LACTOYL ETHANOLAMIDE | 1.00 |
| Cyclomethicone & Dimethiconol | 2.00 |
| Talc | 2.00 |
| Cetearyl Alcohol & PEG-20 Stearate | 1.50 |
| Capric/Caprylic Triglyceride | 1.50 |
| Aluminium Starch Octenylsuccinate | 1.00 |
| Cetearyl Alcohol | 0.60 |
| Triethanolamine | 0.50 |
| Carbomer | 0.20 |
| Preservative | q.s. |

Method:
Add to the water the Carbomer and allow to wet out. Heat to 65° C.
Combine the remaining ingredients and heat to 65° C.
Add the oils to the water phase with high shear.
Stir cool and add preservative and fragrance as required.

Example 9

Deodorising Foot Spray

A deodorising spray to cool and refresh the feet. It provides physiological cooling and emolliency to leave the skin fresh and soft for hours to come.

| Formulation: | % w/w |
| --- | --- |
| Ethanol | to 100.00 |
| Diispropyl Dimer Dilinoleate | 3.00 |
| Menthyl Lactate | 1.50 |
| Fractionated Coconut Oil | 1.00 |
| Triclosan | 0.30 |
| Menthol | 0.20 |
| LACTOYL ETHANOLAMIDE | 1.00 |
| Perfume | q.s. |

Method:
Dissolve the triclosan, menthol and methyl lactate sequentially into the ethanol. Add the remaining ingredients with stirring.
This product can be filled directly into pump sprays, or filled as an aerosol with a butane propellant.

Example 10

Aftersun Cream Gelee

A light cream gel that absorbs without excessive rubbing of tender areas. Its cooling effect is due to Menthyl PCA and Lactoyl Ethanolamine, creating a pleasant feel to skin irritated by the sun.

| | % w/w |
| --- | --- |
| Phase A | |
| Water | to 100.00 |
| Hydroxypropylcellulose | 0.40 |
| Carbomer | 0.20 |
| Phase B | |
| Isostearyl Alcohol | 1.20 |
| Menthyl Pyrrolidone Carboxylate | 1.50 |
| LACTOYL ETHANOLAMIDE | 1.00 |
| Preservative | q.s. |
| Tetrahydroxypropyl Ethylenediamine | 0.30 |
| Perfume | q.s. |

Method
Combine the Hydroxypropylcellulose and water and mix under high shear for one hour so as to allow it to be fully hydrated (i.e. the water must be crystal clear). Add the carbomer and mix.
In a separate vessel, add the Menthyl Pyrrolidone Carboxylate, Lactoyl Ethanolamide and the Tetrahydroxypropyl Ethylenediamine. Once this is mixed, add the preservative, Isostearyl Alcohol and perfume. When this mixture is homogenous, add it to phase A and high shear until smooth. The resulting cream gelee should have a pH within the range 6.0 and 6.5.

Example 11

Refreshing Leg Gel

A light gel that provides a refreshing, cooling feel to 'tired' legs.

|  | % w/w |
| --- | --- |
| Phase A | |
| Water | to 100.00 |
| Ethanol | 40.00 |
| Carbomer | 0.50 |
| Phase B | |
| Menthyl Glyceryl Ether | 1.00 |
| LACTOYL ETHANOLAMIDE | 1.00 |
| Preservative | q.s. |
| Triethanolamine | 0.45 |
| Perfume | q.s. |

Method

Combine the Carbomer to the water and mix under until the carbomer is dispersed. Add the Ethanol and allow any bubbles to separate.

Then stir in the Menthyl Glyceryl Ether, followed by the Lactoyl Ethanolamide, the preservative and the fragrance. Finally, add the triethanolamine and stir until the gel is transparent.

The resulting gel should have a pH within the range 6.0 and 6.5.

The invention claimed is:

1. A method of enhancing the cooling sensation of a physiological cooling agent on skin comprising,
    forming a mixture comprising a physiological coolant and a coolant-enhancing substance and/or physiologically or dermatologically acceptable salts thereof, and
    topically applying said mixture to skin,
    wherein said coolant-enhancing substance is N-lactoyl ethanolamide.

2. The method according to claim 1, wherein the composition is a cosmetic composition.

3. The method according to claim 1, wherein the composition comprises at least 0.01 wt % of the physiological coolant.

4. The method according to claim 1, wherein the composition comprises at least 0.005 wt % of the coolant-enhancing substance.

5. The method according to claim 1, wherein the physiological coolant is selected from the group consisting of menthol, menthyl Pyrrolidone carboxylate, menthyl lactate, menthoxy propanediol, menthone glycerol ketal, isopulegol, methyl di-isopropyl propionamide and ethyl menthane carboxamide and combinations thereof.

6. The method according to claim 1, wherein the physiological coolant is selected from the group consisting of menthyl Pyrrolidone carboxylate, menthyl lactate, menthoxy propanediol, menthone glycerol ketal, isopulegol, methyl di-isopropyl propionamide and ethyl menthane carboxamide and combinations thereof.

* * * * *